(12) United States Patent
Muñoz et al.

(10) Patent No.: US 10,029,394 B2
(45) Date of Patent: Jul. 24, 2018

(54) METHODS FOR FABRICATING IMMOBILIZATION APPARATUS

(71) Applicant: Hermo Medical Solutions, S.L., Saragossa (ES)

(72) Inventors: Javier Muñoz, Saragossa (ES); Toni Climent, Alicante (ES); Luis Monzón, Saragossa (ES); Lucas Pedrajas, Saragossa (ES); Juan Monzón, Saragossa (ES)

(73) Assignee: HERMO MEDICAL SOLUTIONS, S.L., Saragossa (ES)

( * ) Notice: Subject to any disclaimer, the term of this patent is extended or adjusted under 35 U.S.C. 154(b) by 207 days.

(21) Appl. No.: 15/161,272

(22) Filed: May 22, 2016

(65) Prior Publication Data

US 2016/0339607 A1 Nov. 24, 2016

Related U.S. Application Data

(60) Provisional application No. 62/165,438, filed on May 22, 2015.

(51) Int. Cl.
*B29C 33/38* (2006.01)
*A61F 5/058* (2006.01)
(Continued)

(52) U.S. Cl.
CPC .......... *B29C 33/3857* (2013.01); *A61F 5/058* (2013.01); *A61F 5/0585* (2013.01);
(Continued)

(58) Field of Classification Search
CPC ............ B29C 33/3857; B29C 35/0266; B29C 35/0805; B29C 64/35; B29C 64/386;
(Continued)

(56) References Cited

U.S. PATENT DOCUMENTS

| 4,512,340 A * | 4/1985 | Buck .................. A61L 15/12 |
| | | 522/14 |
| 8,838,263 B2 * | 9/2014 | Sivak .................. A61F 5/0111 |
| | | 623/27 |

(Continued)

FOREIGN PATENT DOCUMENTS

| WO | 2014/080217 | 5/2014 |
| WO | 2015/179572 | 11/2015 |
| WO | 2016/071873 | 5/2016 |

OTHER PUBLICATIONS

Connex1 3D Production Systems. Product Website (online). Stratasys, Mar. 18, 2015. (retrieved Sep. 27, 2016). Retrieved from the Internet: <URL:http://www/stratasys.com/3d-printers/production-series/connex1-systems>.

(Continued)

*Primary Examiner* — Matthew J Daniels
*Assistant Examiner* — Leith S Shafi
(74) *Attorney, Agent, or Firm* — Greenberg Traurig, LLP; Chinh H. Pham

(57) ABSTRACT

Devices and methods are provided for fabricating a custom splint for use in an immobilization system. In one aspect, a method for fabricating a splint is provided. The method comprises identifying a region of interest of a limb around which a splint is to be positioned, placing markers about the region of interest on the limb, and scanning the region of interest having the markers to generate data for the splint to be produced.

13 Claims, 11 Drawing Sheets

(51) Int. Cl.
*B29C 35/08* (2006.01)
*B29C 35/02* (2006.01)
*B33Y 10/00* (2015.01)
*B33Y 50/02* (2015.01)
*B33Y 40/00* (2015.01)
*B33Y 80/00* (2015.01)
*B29C 64/106* (2017.01)
*B29C 64/386* (2017.01)
*B29C 64/35* (2017.01)

(52) U.S. Cl.
CPC ...... *A61F 5/05866* (2013.01); *B29C 35/0266* (2013.01); *B29C 35/0805* (2013.01); *B29C 64/106* (2017.08); *B29C 64/35* (2017.08); *B29C 64/386* (2017.08); *B29C 2033/3871* (2013.01); *B29C 2035/0827* (2013.01); *B33Y 10/00* (2014.12); *B33Y 40/00* (2014.12); *B33Y 50/02* (2014.12); *B33Y 80/00* (2014.12)

(58) Field of Classification Search
CPC .......... B29C 64/106; B29C 2035/0827; B29C 2033/3871; B29C 64/00; A61F 5/05866; A61F 5/058; A61F 5/0585; A61F 2/5046; A61F 2002/5053; A61F 2/7812; A61F 2/30942; A61F 2/52; A61F 2002/505; A61F 2240/004; A61F 2/2415; A61F 2002/30948; A61F 2002/30952; B33Y 80/00; B33Y 10/00; B33Y 40/00; B33Y 50/02; B29L 2031/7532; B29L 2031/753
USPC .......... 264/222, 223, 16, 401, 497, DIG. 30; 425/2; 623/901; 249/55; 2/162
See application file for complete search history.

(56) References Cited

U.S. PATENT DOCUMENTS

| | | | |
|---|---|---|---|
| 9,532,917 B2* | 1/2017 | Summit | A61F 5/013 |
| 2005/0015172 A1* | 1/2005 | Fried | A61F 5/058 |
| | | | 700/118 |
| 2007/0016323 A1* | 1/2007 | Fried | A61F 5/05 |
| | | | 700/118 |
| 2010/0138193 A1* | 6/2010 | Summit | G06F 17/50 |
| | | | 703/1 |
| 2014/0081190 A1* | 3/2014 | Summit | A61F 5/013 |
| | | | 602/19 |
| 2016/0374431 A1* | 12/2016 | Tow | A43B 17/003 |
| | | | 36/43 |

OTHER PUBLICATIONS

PCT International Search Report and Written Opinion issued is International Application No. PCT/US2016/033685 dated Oct. 20, 2016.

* cited by examiner

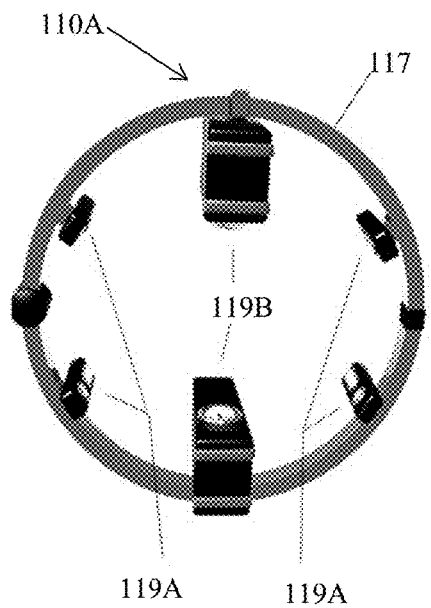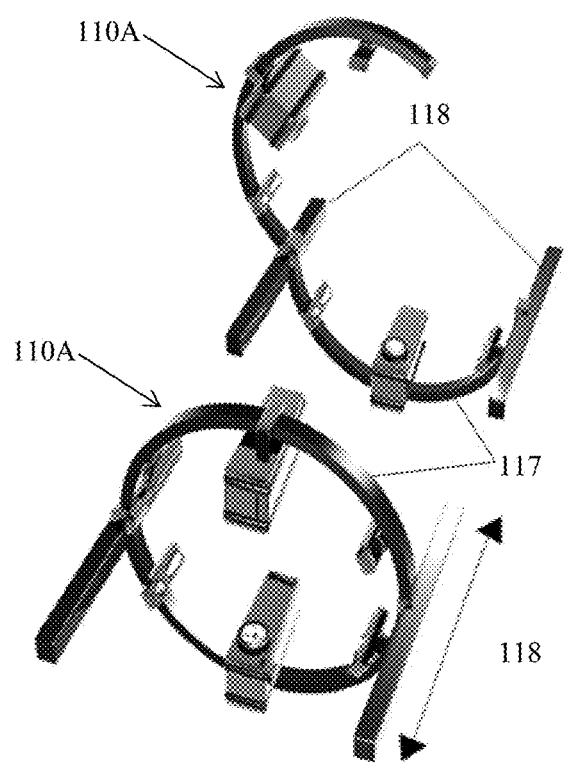
FIG. 1B
FIG. 1C

METHODS FOR FABRICATING IMMOBILIZATION APPARATUS

CROSS REFERENCES TO RELATED APPLICATIONS

This application claims priority to and the benefit of U.S. Provisional Application Ser. No. 62/165,438, filed May 22, 2015, the disclosure of which is hereby incorporated herein by reference in its entirety.

FIELD

The present disclosure relates to methods for fabricating a customized splint.

BACKGROUND

When bones are fractured, cracked, or ligaments are lengthened or ruptured, an orthopedic cast or splint is often applied to the injured area to immobilize the injured joints and muscles partially or entirely.

One issue with using splints or casts is that they can often not be easily applied to and removed from the injured area. For example, application of a plaster bandage can be complicated, and once the plaster bandage is placed over the injured area, it typically remains in place for about five weeks, which can promote the growth of mold or infectious bacteria. Further, the process of the removing cast by using a saw can generate dust, which can cause problems to the injured area.

Moreover, when the cast is applied around the injured area, it can be difficult to initiate early joint movement, and inaccurate or abnormal fixation cannot be checked through intermediate inspections due to the cast covering the injured area. Even after the splint or cast is removed, it can often be replaced with another type of splint, for the rehabilitation phase and can result in similar issues noted above. Since rehabilitation cannot be started until bone immobilization is completed, the application of a splint to the injured area can lead to muscular atrophy. Long recovery times can result in unnecessary costs to the injured person, since there are a number of the healthcare providers and other individuals (e.g., patients, employers, rehabilitation centers and health insurance companies) involved in the recovery process.

Thus, there is a need for an immobilization system that can overcome these and other issues.

SUMMARY

In one aspect, a method for fabricating a splint is provided. The method comprises identifying a region of interest of a limb around which a splint is to be positioned, placing markers about the region of interest on the limb, and scanning the region of interest having the markers to generate data for the splint to be produced.

In some embodiments, the markers aid in detecting features or target areas located on the limb to which pressure or treatment needs to be focused. In some embodiments, the markers aid in modeling the splint to conform to the identified features on the region of interest where the splint needs to target. In some embodiments, the markers aid to demarcate the borders of the splint. In some embodiments, the image capture devices are provided to capture images circumferentially about the limb.

In some embodiments the method can further comprise, positioning a photo-polymeric material around the region of interest, projecting an image of a splint generated from the scanned data on to the photopolymeric material, curing the imaged area of the photopolymeric material and removing the remaining uncured portions to provide a splint. In some embodiments, the photo-polymeric material is pliable to conform about the limb. In some embodiments, the photo-polymeric material includes a photo-curable material. In some embodiments, the image of the splint is projected circumferentially about the region of interest of the limb. In some embodiments, the splint is cleaned once the uncured portions are removed.

In some embodiments, the method can further comprise using the data generated from the scan to deposit a polymeric material layer by layer into the shape of the splint and curing the deposited polymeric material to provide the splint. In some embodiments, the deposition of the polymeric material follows a desired pattern of the splint to be produced. In some embodiments, curing includes each layer of polymeric material. In some embodiments, the polymeric material is cleaned with a solvent. In some embodiments, cleaning includes each layer of polymeric material.

BRIEF DESCRIPTION

The presently disclosed embodiments will be further explained with reference to the attached drawings. The drawings shown are not necessarily to scale, with emphasis instead generally being placed upon illustrating the principles of the presently disclosed embodiments.

FIGS. 1B-1C illustrate a scanner for use with fabrication system, according to embodiments of the present disclosure;

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present disclosure is directed to an immobilization system designed to improve processes for treating an injured area. Immobilization system can improve patient quality of life by improving the patient's healing processes, through the use of a custom splint. The custom splint, in one embodiment, can be generated through the use of a fabrications system as described below.

Splint Fabrication System

Figure 1A:
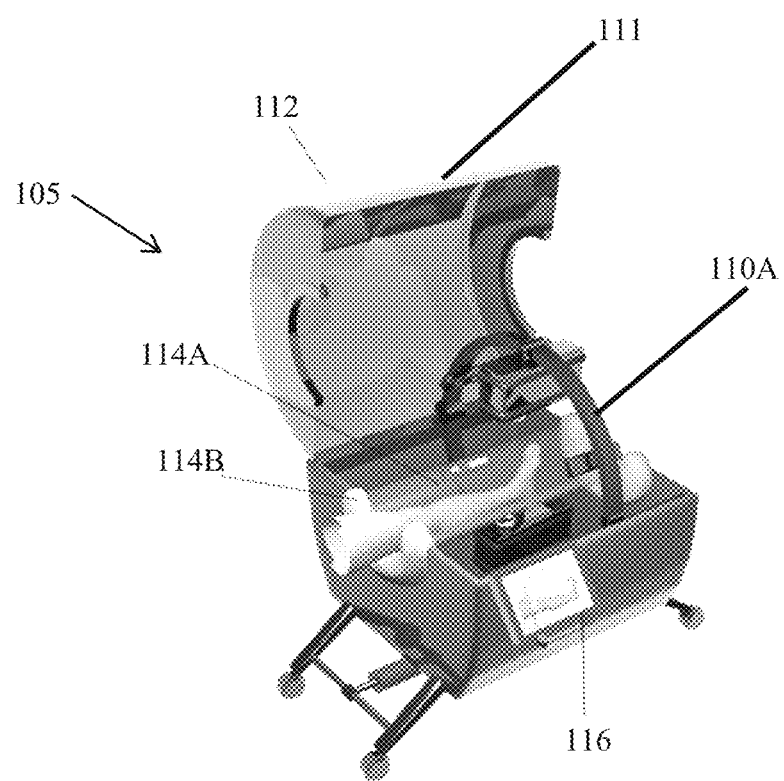
FIG. 1A, illustrates a fabrication system for generating a customized splint, according to embodiments of the present disclosure.

With reference to FIG. 1A, fabrication system 105, in one embodiment, includes a 3D scanner 110A for generating a three dimensional image of a region of interest (i.e. injured area) on a limb. Fabrication system 105 can also include a light filter 112 on lid 111, supports 114A and 114B, and a control screen 116 to control the operation of the system 105.

FIG. 1B and FIG. 1C illustrate, in one embodiment, scanner 110A for use with system 105. As illustrated, scanner 110A includes one or more image capture devices 119A positioned about ring 117 that is designed to move along rail 118. In one embodiment, movement of movement of ring 117 can be effectuated by a stepper motor (not shown). Scanner 110A, in one embodiment, can also be provided with one or more cameras 119B.

Figure 2A:
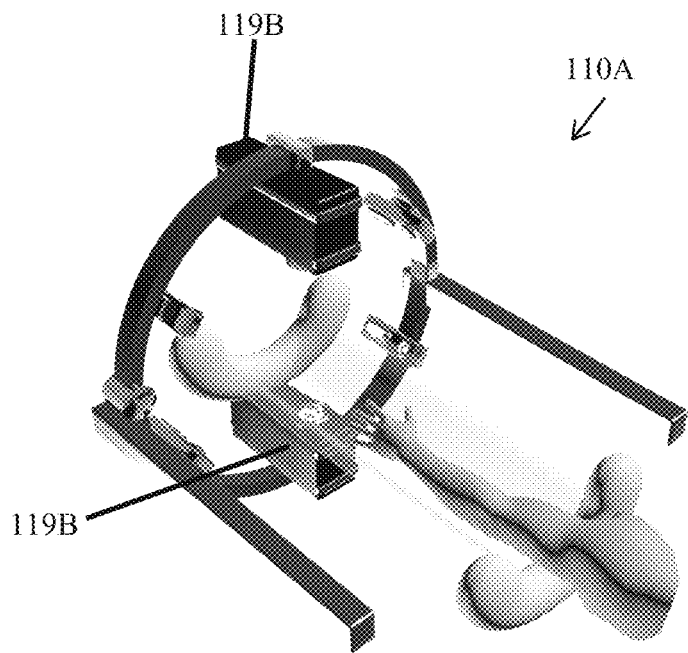
FIGS. 2A-2B illustrate an example of patient orientation during the scan procedure, according to embodiments of the present disclosure.
Figure 2B:
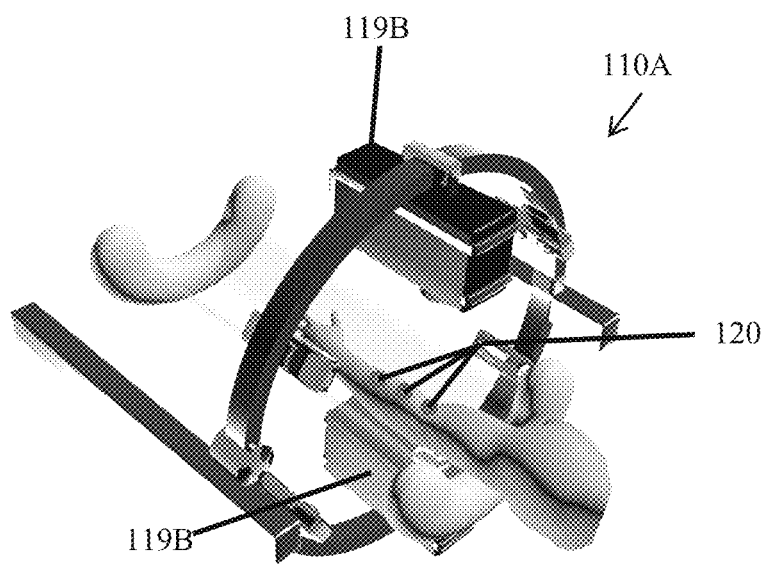

FIGS. 2A and 2B illustrate an example of a patient orientation during the scan procedure. FIG. 2A illustrates an injured body part, such as a limb, being placed on supports 114A and 114B in preparation for scanning by 3D scanner 110A. Once on support 114A and 114B, control screen 116 can be accessed to initiate 3D scanner 110A for scanning. FIG. 2B illustrates the injured body part being scanned about the limb circumferentially by the 3D scanner 110A.

For purposes of the present invention, the 3D scanner 110A can be configured to generate a substantially true image of a limb. 3D scanner 110A can be configured to interface with a computer to obtain, store, and process scanned image data. Scanned image data, in one embodiment, maybe processed using software that is capable of analyzing the data and identifying injured areas. It is contemplated that 3D scanner 110A can be scaled to allow for applications that require small dimensions, for example, mobile applications.

In some embodiments, the 3D scanner 110A can be configured to obtain color, infrared and depth information from the images collected from a scan. To that end, in one embodiment, the 3D scanner 110A can be configured with two cameras 119B. For example, a suitable camera for use with 3D scanner 110A can be the Intel RealSense SR300 camera. It is contemplated that additional configurations of cameras, infrared projectors or other imaging devices can be utilized to obtain scan data. Depending on the application, these devices can be fixedly positioned about ring 117 or can be designed to circumferentially move along ring 117. In this way, the 3D scanner 110A is capable of generating a substantially true image of a limb, and subsequently model a custom made splint based on the image data of the limb.

The 3D scanner 110A, in an embodiment, can be calibrated according to protocols using motion detection, or standards of known length to detect and correct discrepancies in data acquisition and printing. These calibration methods are well known in the art.

To facilitate the fabrication of a splint that can be customized to each individual patient, in accordance with an embodiment of the present invention, markers 120 can be placed on the limb around the injured area to help scanner 110A of the fabrication system 105 in detecting features or target areas located on the limb to which treatment, such as that provided by a therapeutic device (i.e., electrotherapeutic device) needs to focus. The markers 120, according to embodiments of the present invention, can be of different shapes, colors, and/or patterns. The markers 120, according to embodiments of the present invention, can be used to identify a site of an injury, or demarcate the desired borders for the to-be-fabricated splint. Markers 120 can also be used to provide perforation patterns or openings in the splint to allow circulation of air to the injured area to facilitate healing. Markers 120 can also be used to identify areas within the splint where thickness needs to be increased or decreased, or where the shape of the splint needs to be altered to increase or decrease pressure applied to the injured area. Markers 120 can further be used to identify where on the splint a therapeutic device, such as an electrotherapeutic device (discussed below), can be placed for treatment. Furthermore, the use of markers 120 can help, for example, to create a structural offset, spacing, or gaps between the limb and splint. The structural offset can enable the splint to, for example, reduce pressure to a target area of the limb or, accommodate a foam insert to reduce irritation, chafing, or discomfort.

The markers 120, in one embodiment, can be applied to the limb before scanning by scanner 110A. With the markers 120 in position on the limb, control screen 116 can be accessed to initiate a 3D scan by scanner 110A. As the limb is scanned, the position of the markers 120 can be captured along with the limb data as digital 3D scan data. As the digital 3D scan occurs, scanner 110A also receives information corresponding to the color spectrum, infrared profile, and depth profile of the scan, which can then be included in the 3D digital scan data file. The digital 3D scan data, including data from the markers 120, can then be transferred to a computing device and processed to construct a 3D model of a to-be-fabricated splint that conforms to the features on the limb or areas of interest identified by marker 120 where the to-be-fabricated splint needs to target.

It should be appreciated that the 3D scanned data can be processed through software of the present invention to represent a 3D model of a to-be-fabricated splint on a three dimensional coordinate system. Such a rendering of a 3D representation using the process of the present invention, can allow the user to select and manipulate the properties of specific regions on the splint prior to fabrication. The processed 3D scan data can, in one embodiment, be used in connection with various fabrication methods, for example, traditional 3D printing processes, or in connection with any fabricating devices coupled to computer interfaces.

Figure 3:
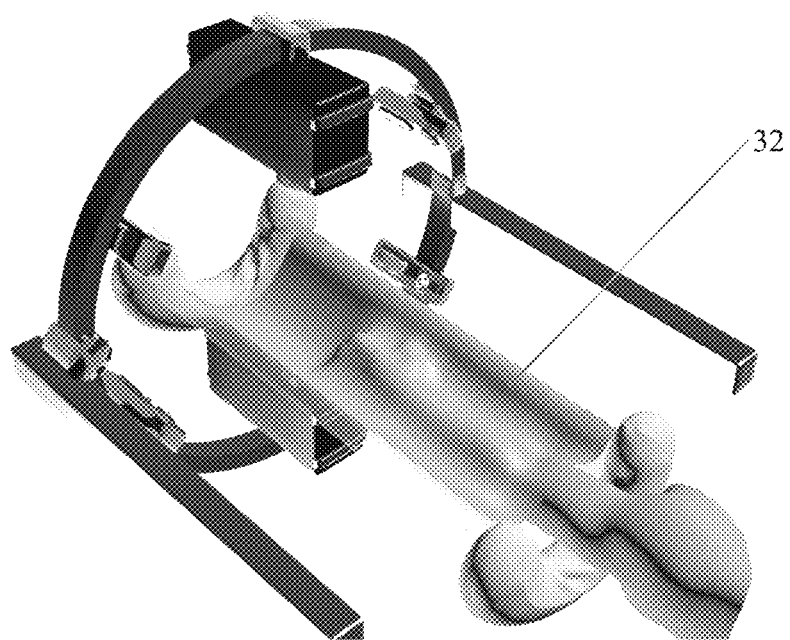
FIG. 3 illustrates a sheet of photo-polymeric placed over an injured body part, according to embodiments of the present disclosure.

Once the limb has been scanned, looking now at FIG. 3, in one embodiment of the present invention, a photo-polymeric material 32, and may be place over the injured body part. The photo-polymeric material 32, in an embodiment, can be a pliable, photo-curable polymeric material, such as PLA polymer, or any similar FDA approved materials. In one embodiment, the photo-polymeric material 32 can be a translucent material, such that the light can penetrate and cure the photo-curable polymeric material 32.

Figure 4A:
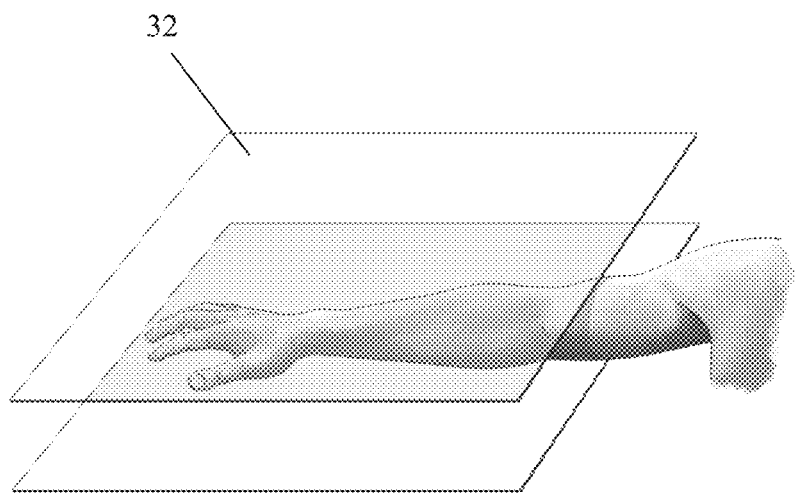
FIGS. 4A-4B illustrate the placement of a sheet of photo-polymeric material over the injured body, according to embodiments of the present disclosure.
Figure 4B:
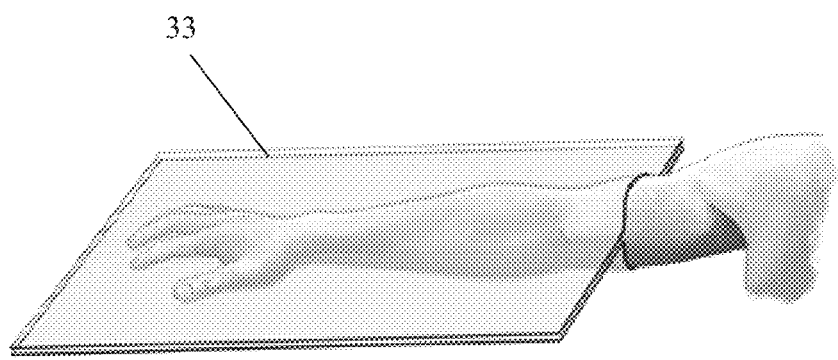

Placement of the photo-polymeric material 32 over the injured body part can be accomplished, in one embodiment, as illustrated in FIGS. 4A-4B by placing the injured body part between two sheets 33 of photo-polymeric material 32, such that one sheet of photo-polymeric material 32 is placed above the injured limb and another sheet of photo-polymeric material 32 placed below the injured limb. Both sheets 33 of photo-polymeric material 32, in an embodiment, can be permitted to approach each other and stick together, thus enclosing the limbs surface and adopting its volume. It should be appreciated that the sheets 33 can be secured to one another by any manner known in the art. It should be noted that although two sheets 33 of photo-polymeric material 32 are referenced in an embodiment, only one sheet 32 may be needed. In such a situation, the sheet 32 may be placed over the injured body part and then wrapped around the limb.

With the sheets photo-polymeric material 32 placed over the injured body part, pressure can then be gently applied against the injured body part to conform the sheets of photo-polymeric material 32 to the limb. To the extent desired, another scan of the injured limb maybe executed in order to verify any variation in the injured limb's position, to ensure accuracy of the 3D scanner data to be used in fabrication.

Figure 5A:
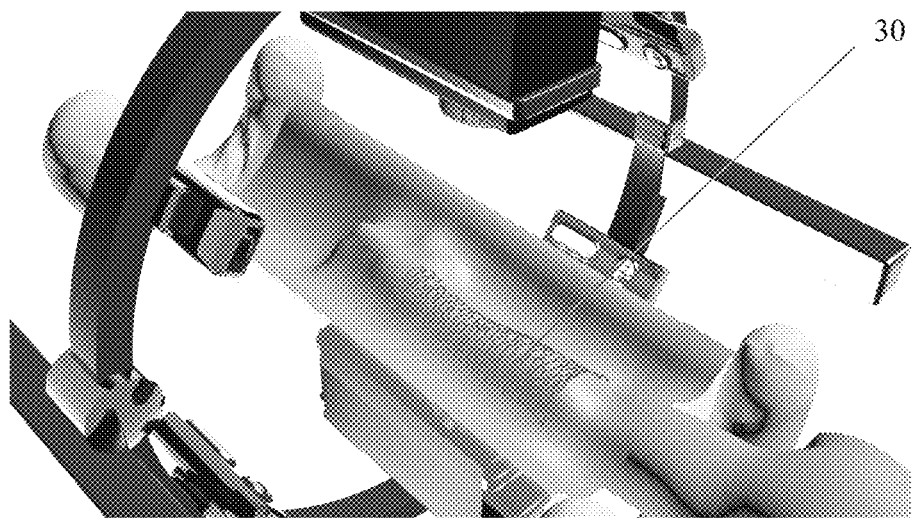
FIGS. 5A-5B illustrate the projected image of a to-be-fabricated splint onto the surface of the photo-polymeric material, according to embodiments of the present disclosure.
Figure 5B:
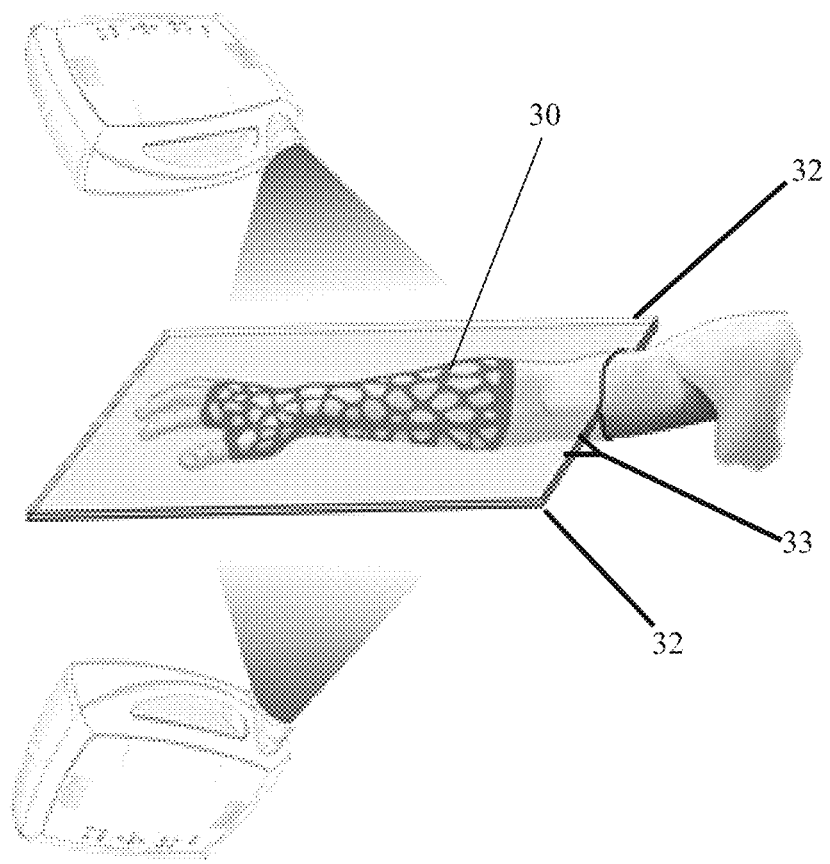

Next, looking now at FIG. 5A, an image 30 of a to-be-fabricated splint may then be projected by scanner 110A using, for example, UV light, onto the surface of the photo-polymeric material 32. In one embodiment, as shown in FIG. 5B, image 30, having a pattern corresponding to the digitized splint processed from the 3D scanner data, may be projected from above and below (i.e., circumferentially) about the region of the injured limb on to the surface of the sheets of photo-polymeric material 32 to cure the photo-polymeric material in each sheet 32. It should be appreciated that a multitude of curable light technologies including a DLP projector or light lamp may be used to cure the photo-polymeric materials.

Figure 5C:
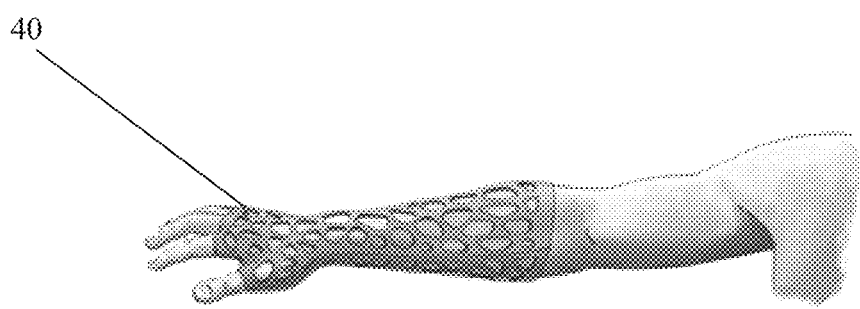
FIG. 5C illustrates a newly formed splint, according to embodiments of the present disclosure.

In an embodiment, the area of the photo-polymeric material 32 onto which UV light is projected is cured, for example in about 30 seconds or more, to form a shape of splint 40. In one embodiment, the uncured portions of the sheet of photo-polymeric material 32, can thereafter be removed to provide the customized splint 40, as shown in FIG. 5C.

It should be appreciated that customized splint 40 may need to have different properties, as will be described below, to accommodate different limb shape, profile, and/or injuries suffered by different patients. To that end, in some embodiments, the photo-polymeric material 32, can be provided with different properties, for example, throughout sheet 32, along the length of sheet 32, along the thickness of sheet 32, in each layer of sheet 32 (if sheet 32 is made from multiple layers), or a combination thereof, so that once the photo-polymeric material 32 is cured, the desired property or properties can be imparted to the resulting customized splint 40.

Figure 6:
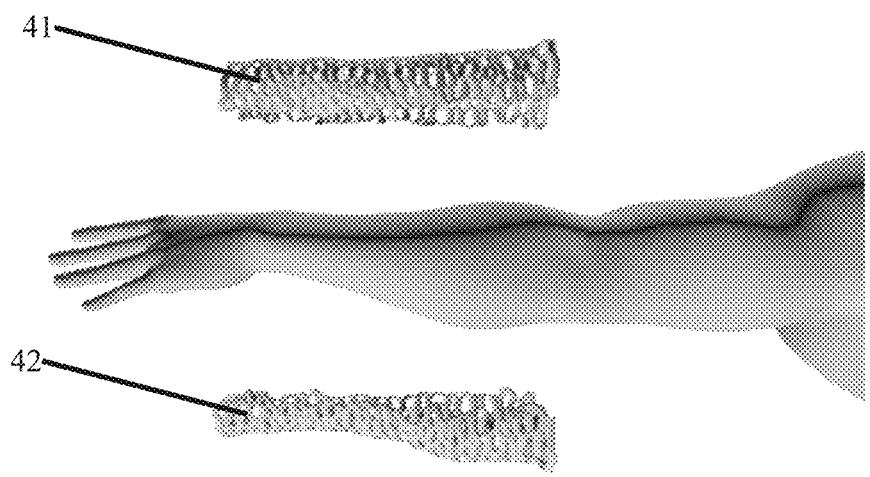
FIG. 6 illustrates two halves of the splint shown in FIG. 5C, according to embodiments of the present disclosure.

The customized splint 40, thereafter, can be removed from the limb for cleaning. It should be appreciated that by using two sheets of photo-polymeric material 32 placed above and below the limb, once splint 40 is formed, there is provided an upper half 41 and a bottom half 42 that can be naturally separated along an area where the two photo-polymeric sheets 33 initially adjoin, as illustrated in FIG. 6. In one embodiment, the upper half 41 and the lower half 42 of splint 40 may be separated and cleaned with biocompatible solvents, such as ethanol, to eliminate uncured portions of the photo-polymeric material 32.

As an alternative to the use of one or more sheets or photo-polymeric material 32 to fabricate customized splint 40, data obtained from the 3D scan can be utilized to fabricate the customized splint 40 by a 3D printing process. In one embodiment, instead of projecting the image of splint 40 onto the limb, as noted above, a 3D printing process may be utilized to spray or deposit (i.e., print), layer by layer, the material to form splint 40 following the desired shape and pattern, such as the pattern shown in FIG. 5C, directly onto the limb. The material, in one embodiment, can be a polymeric material such as that used above, or any other biocompatible material that can be directed through a 3D printing nozzle. To facilitate the deposition of the material on a layer by layer basis, such deposition, in accordance with in embodiment of the present invention, can be accomplished by utilizing one or more 3D printing nozzles. In one embodiment, it is contemplated that as each layer is deposited (i.e., printed), curing of the deposited material can be carried out before or as the next layer is deposited. In an embodiment, cleaning of each layer for example, by use of a solvent or solvents similar to that noted above, can be carried before or as the next layer is deposited as needed.

Of course, should it be desired, splint 40 may not need to be printed directly on the limb of the patient. Rather, splint 40 may first be printed and thereafter be placed onto the limb around the injured area.

It should be appreciated that various 3D printing protocols can be utilized in connection with the fabrication of customized splint 40 of the present invention. Examples of 3D printing protocols include 3D printing via Stereolithography (SLA), Digital Light Processing (DLP), Fused deposition modeling (FDM), Selective Laser Sintering (SLS), Selective laser melting (SLM), or Electronic Beam Melting (EBM).

The fabricated customized splint 40 may thereafter be used in an immobilization system 100 (see FIG. 7) designed to improve processes for treating broken bones and muscle injuries.

Immobilization System

Figure 7:
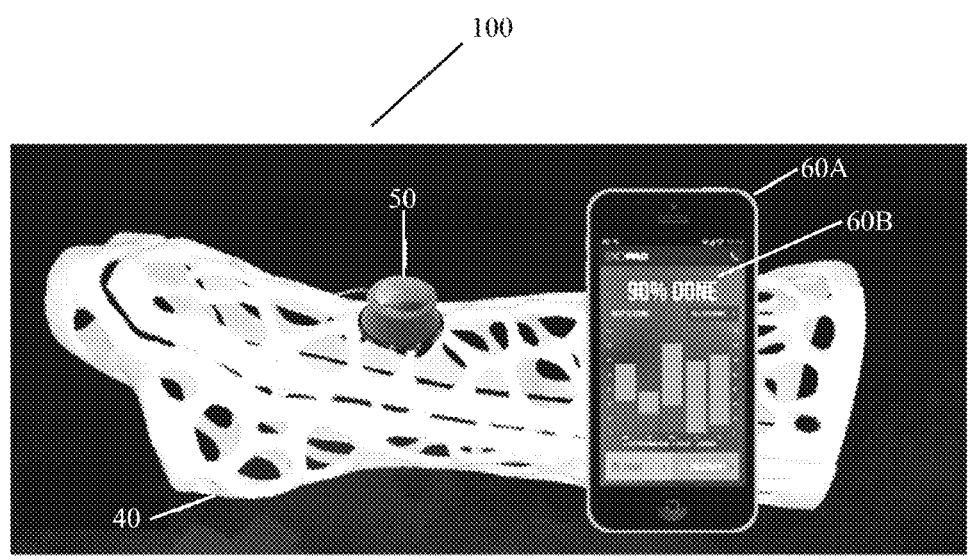
FIG. 7 illustrates components of an immobilization system according to embodiments of the present disclosure.

Referring now to FIG. 7, immobilization system 100 in various embodiments, may include a custom manufactured splint 40 for immobilizing an injured body part, a wireless interface 60A, and one or more therapeutic devices 50 coupled to splint 40. The therapeutic device 50 can effectuate healing of a target area by communicating with the wireless interface 60A to deliver stimulation to a targeted area.

Figure 8A:
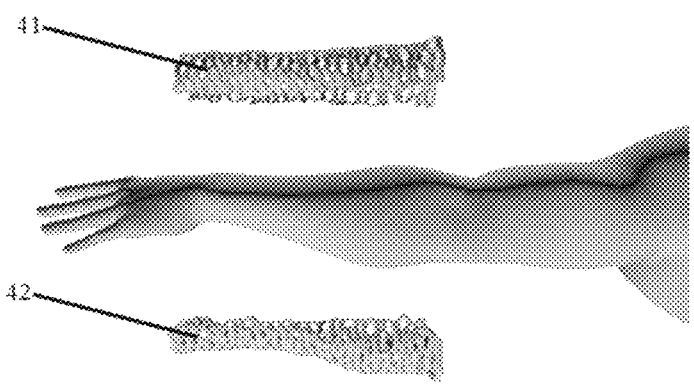
FIGS. 8A-8B illustrate a splint used in connection with the immobilization system in FIG. 7 in an unassembled state and assembled sate attached to a body part, according to embodiments of the present disclosure.
Figure 8B:
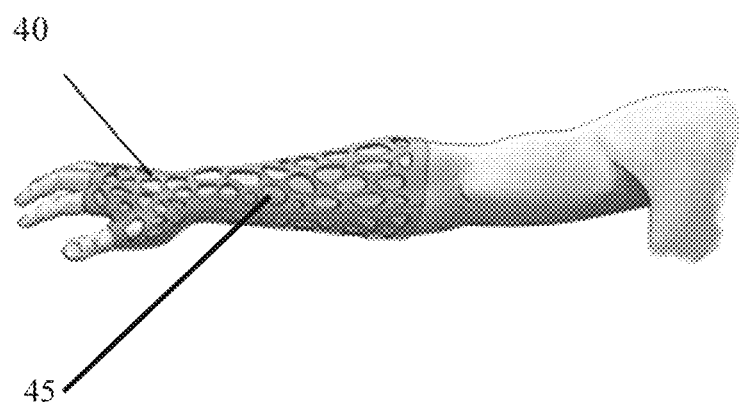

Referring now to FIG. 8A and FIG. 8B, splint 40, in one embodiment, may be configured for immobilizing an injured body part to promote proper healing. Splint 40, as noted above, can be made from one or more materials that are FDA approved, such as medical grade PLA polymer. In one embodiment, the material can be waterproof to minimize deterioration of splint 40 when exposed to perspiration, water or the like. Further, the material can be opaque, transparent, or translucent to permit light to pass through promote healing to the injured area. The material, in an embodiment, can be relatively stiff but can still be imparted with elasticity to permit some movement around the injured area. It is contemplated that the elasticity ranges can also provide the splint 40 with the capability to adopt the limb's shape and fit around the limb. The customized splint 40 may have an overall weight up to approximately 150 grams or less, 200 grams or less, 300 grams or less, 350 grams or less, 375 grams or less, 400 grams or less, 450 grams or less, and 500 grams or less. It is contemplated that the customized splint 40 may be perforated, and may include one or more patterns having uniform spaces 45, non-uniform spaces or some combination thereof in order to facilitate aeration to the injured area to minimize infection, as well as growth of mold and bacteria.

FIGS. 8A and 8B illustrate, in an embodiment, splint 40 having a multi-piece construction. FIG. 8A shows splint 40 unassembled while, FIG. 8B shows splint 40 assembled around the injured area. It should be appreciated that a multi-piece construction can provide for ease of fitting the splint 40 to a patient and ease of removal from the body part without having to disrupt the structure of the splint 40. It should be appreciated that splint 40 can also be one piece in design that can be wrapped around an injured area.

Figure 9A:
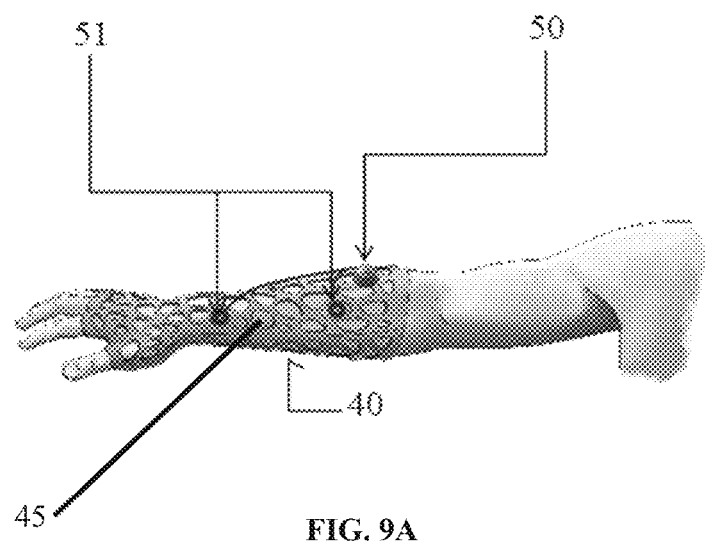
FIGS. 9A-9B illustrate a therapeutic device mounted onto the splint, according to embodiments of the present disclosure.
Figure 9B:
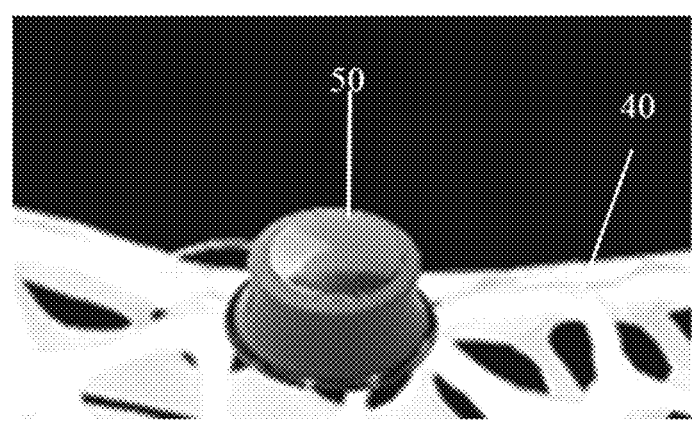

The spaces 45, in some embodiments, may provide for placement of one or more therapeutic devices, such as stimulator 50, directly against skin, while proving structure for securing the stimulators in place. As shown in FIG. 9A, a honeycomb structure provides openings 45 in the splint 40 that allow for therapeutic device 50 to be placed directly against the skin, while, as shown in FIG. 9B, providing local structure around therapeutic device 50 to secure the therapeutic device 50 in place. Splint 40, in an embodiment, may be further constructed with a grid pattern (not shown), where the grid pattern can be structured and arranged to provide one or more attributes. For example, the attributes may include having sections within the grid system that could include varying diameters of the material of the splint 40, varying space dimensions that are uniform, non-uniform or some combination thereof. It is contemplated that the grid system for the splint 40 can be structured to provide different ranges of elasticity within areas of the splint 40. At least one aspect of the grid system can include improved skin aeration during the time of healing, and can minimize itching and allergies, as well as provide access for medical staff to administer healthcare related activities, among other things.

Splint 40 can also be provided with multiple regions where the shape, thickness or size is varied to apply or relieve pressure at or around the injury site to facilitate the healing process and provide comfort to the patient. For example, in some embodiments, the shape of the splint 40 can be designed to conform or avoid contours or feature of the limb. In other embodiments, the thickness of the splint 40 can be increased to apply more pressure to the limb, or the thickness of the splint 40 can be decreased to reduce the pressure to the limb.

Splint 40, in various embodiments, may be custom manufactured using 3D technology to match the shape and size of the injured body part. In one embodiment, data obtained, for example, from a 3D scan of a limb or region of the body, can be used to model and to create a custom-fitting splint 40. In particular, the 3D scanned data can be digitally processed to create a digital representation of the limb or body region. Subsequently, in one embodiment, the splint 40 may be fabricated using a process of the present invention. In particular, the 3D scanned data may be utilized to generate a map of the customized splint 40. The map of customized splint 40 can then be projected onto a photo-curable polymer, where the polymer reacts to the projection of light, to cure the polymer in the shape of splint 40. The uncured portions are then removed and used to provide the desired customized splint 40.

Still referring to FIGS. 9A and 9B, therapeutic device 50, in various embodiments, may be configured for providing therapeutic stimulation throughout the healing process. Such stimulation can be utilized to reduce fatigue, as well as stimulate bone and muscle growth to the injured area.

In some embodiments, the therapeutic device 50 can be configured to allow control of the intensity, frequency, and duration of the stimulation. By varying the output of therapeutic device 50, user defined settings can be utilized to tailor fit treatment as needed.

As illustrated in FIG. 9A, splint 40 can have two electrodes 51, to which signals can be transmitted to stimulate an injured area. It has been contemplated that depending upon the requirements of a treatment, splint 40 can be configured to accommodate a multitude of electrodes 51 and therapeutic devices 50 to stimulate the injured area.

Many patients experience atrophy of immobilized muscles over a period of time. By measuring the muscle mass index, atrophy can be monitored to guide treatment plans, and to determine the level of stimulation provided, thereby minimizing or completely preventing muscle atrophy. Therapeutic device 50, in an embodiment, may also be configured as a sensor, for example, to measure the muscle mass index of the injured area. Monitoring the muscle mass index of a patient can be accomplished by sending progress data from therapeutic device 50 to wireless interface 60A. The level of stimulation delivered by therapeutic device 50 can be modulated, for instance by a clinician or patient, to meet the need of the treatment plan. Of course, if desired, therapeutic device 50 can be provided with other sensor capabilities or alternative sensor devices can be used.

In various embodiments, therapeutic device 50 can be attached to splint 40 in any suitable manner. For example, in some embodiments, a thread, clip, screw fasteners, rivets, and/or snap-fits may be used to attach therapeutic device to splint 40. In other embodiments, therapeutic device 50 can be attached to splint 40 by adhesives, bonding materials, or by being magnetically fastened.

With reference again to FIG. 7, wireless interface 60A of the present invention may also include a smart application 60B to communicate with therapeutic device 50. Wireless interface 60A in one embodiment, may be a smart device 60A, which can act as a processing unit while providing monitoring and delivery of a treatment. Additional examples of smart device 60A can include a smart phone, tablet, notebook, personal computer, a cloud network 80A based service application or any electronic devices having input output functions.

In accordance with one embodiment, smart device application 60B can communicate with the therapeutic device 50, while wireless interface 60A acts as a processing unit for data. Suitable wireless communication modalities include Wi-Fi, mobile technologies such as (G, E, 3G, H, H+ and 4G), Bluetooth or other protocols. The application 60B can utilize data encryption to provide a secure communication channel.

Application 60B can also be designed to communicate with medical software packages or other similarly related smartphone applications via the internet 80B and/or a cloud network 80A. For example, in an embodiment, application 60B also allows the physician to provide personalized care for patients by providing, for example, online treatment design, monitoring and modification of the treatment process at any time, remote control and monitoring of therapeutic device 50, analysis of progress data for each patient, and the ability to conduct a remote assessment of the patient using the phone's camera.

The present disclosure is directed to an immobilization system designed to improve processes for treating an injured area. Immobilization system 100 can improve patient quality of life by improving the patient's healing processes, as to eliminate unnecessary visits to hospitals or clinics, as well as saving time and money to all parties involved in the course of rehabilitation. Embodiments of immobilization system 100 of the present disclosure can be used in different industries and technologies including, the health industry, medical device technologies, space technologies, aquatic technologies, robotic system technologies and the like. Immobilization system 100 of the present disclosure can be used in creating stencils or insoles, armature or custom body protections. It is possible for the new immobilization system 100 of the present disclosure can be used in custom technology applications for to devices, such as for creating rapid protective cases, i.e. iPhone case, or a car cover replacement, a helmet or a glove.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It will be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

The invention claimed is:

1. A method for fabricating a splint, the method comprising:
    identifying a region of interest of a limb around which a splint is to be positioned;
    placing markers about the region of interest on the limb around which the splint is to be placed; and
    scanning the region of interest having the markers to generate data for the splint to be produced that conforms to features on the region of interest positioning a photo-polymeric material around the region of interest;
    Projecting on to the photopolymeric material, an image of a splint generated from the scanned data; and
    Curing the imaged data of the photopolymeric material and removing the remaining uncured portions to provide a splint.

2. A method according to claim 1, wherein, in the step of placing, the markers help in detecting features or target areas located on the limb to which pressure or treatment needs to be focused.

3. A method according to claim 1, wherein, in the step of placing, the markers aid in modeling the splint to conform to the identified features on the region of interest where the splint needs to target.

4. A method according to claim 1, wherein, in the step of placing, the markers aid to demarcate the borders of the splint.

5. A method according to claim 1, wherein, in the step of scanning, image capture devices are provided to capture images circumferentially about the limb.

6. A method according to claim 1, wherein in the step of positioning, the photo-polymeric material is pliable to conform about the limb.

7. A method according to claim 1, wherein the step of projecting, the image of the splint is projected circumferentially about the region of interest of the limb.

8. A method according to claim 1, further comprising cleaning the splint once the uncured portions were removed.

9. A method according to claim 1, further comprising:
    using the data generated from the scan, depositing, layer by layer, a polymeric material into a shape of the splint to be produced; and
    curing the deposited polymeric material to provide the splint.

10. A method according to claim 9, wherein the step of depositing includes allowing the deposition of the polymeric material to follow a desired pattern of the splint to be produced.

11. A method according to claim 9, wherein the step of curing includes curing each layer of polymeric material.

12. A method according to claim 9, further including cleaning the polymeric material with a solvent.

13. A method according to claim 11, wherein the step of cleaning includes cleaning each layer of polymeric material.

\* \* \* \* \*